United States Patent [19]

Murata

[11] Patent Number: 4,689,044
[45] Date of Patent: Aug. 25, 1987

[54] FIRST-AID ADHESIVE BANDAGE

[75] Inventor: Takaaki Murata, Kumamoto, Japan

[73] Assignee: ASO Pharmaceutical Co., Ltd., Kumamoto, Japan

[21] Appl. No.: 796,822

[22] Filed: Nov. 12, 1985

Related U.S. Application Data

[63] Continuation of Ser. No. 663,918, Oct. 23, 1984, abandoned.

[51] Int. Cl.$^4$ .............................................. A61F 7/02
[52] U.S. Cl. ..................................... 604/306; 128/155
[58] Field of Search ............................... 604/306, 307; 128/132 R, 155, 156

[56] References Cited

U.S. PATENT DOCUMENTS

| | | | |
|---|---|---|---|
| 2,489,675 | 11/1949 | Roberts | 604/306 |
| 2,579,403 | 12/1951 | Slomowitz | |
| 2,595,606 | 5/1952 | Pohjola | 604/306 |
| 2,714,382 | 8/1955 | Alcala | |
| 3,297,032 | 1/1967 | Antonik | 604/306 |
| 4,117,841 | 10/1978 | Perrotta et al. | 604/306 |
| 4,390,519 | 6/1983 | Sawyer | 128/156 |

FOREIGN PATENT DOCUMENTS

| | | | |
|---|---|---|---|
| 82402254.5 | 6/1983 | European Pat. Off. | |
| 0090564 | 10/1983 | European Pat. Off. | 128/155 |
| 58-99957 | 9/1983 | Japan | 13/2 |
| 837226 | 3/1957 | United Kingdom | 81/2 |

Primary Examiner—Stephen C. Pellegrino
Attorney, Agent, or Firm—Armstrong, Nikaido, Marmelstein & Kubovcik

[57] ABSTRACT

This invention provides a first-aid adhesive bandage comprising a bandage main body having an adhesive coating on its upper surface, a pad affixed to the upper surface of the main body, a container having a medicinal agent enclosed therein and at least one peel sheet temporarily affixed to the adhesive coating of the main body and holding the container in place on or over the pad, the container including a blister portion, a flange extending horizontally outward from the lower end of the blister portion, a bottom wall made of a thin sheet and closing the bottom opening of the blister portion, and a projection extending downward from the central portion of the container top wall for rupturing the thin sheet by depressing the top wall, the blister portion having the medicinal agent enclosed therein, the projection having a lower end in contact or in proximity to the thin sheet, the peel sheet having the container held in position on or over the pad such that the blister portion of the container is exposed above the peel sheet to extend into a side opposed to the pad, the flange of the container is held in contact with the peel sheet and the bottom wall of the container lies on or over the pad.

14 Claims, 7 Drawing Figures

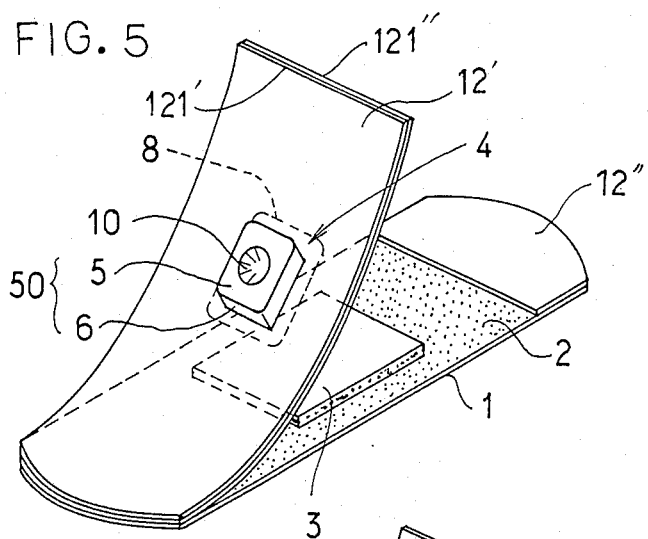
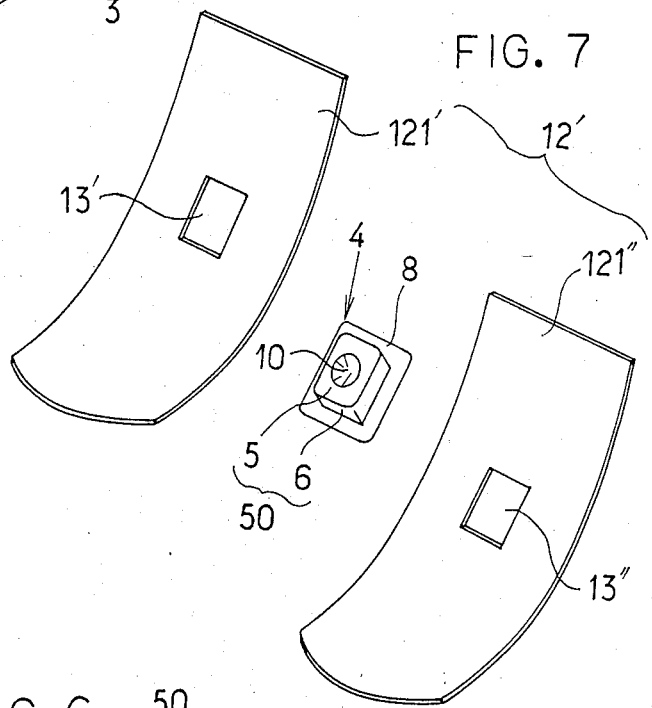
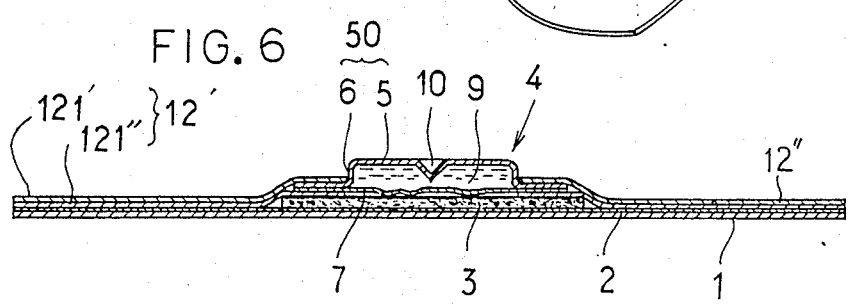

FIRST-AID ADHESIVE BANDAGE

This is a continuation of application Ser. No. 663,918, filed Oct. 23, 1984, now abandoned.

This invention relates to an improvement in first-aid adhesive bandages wherein a medicinal agent can be applied to or caused to impregnate a pad when required.

Various first-aid adhesive bandages have heretofore been provided. For example, adhesive bandages are in wide use which comprise a pad of gauze or the like affixed to the central portion of the adhesive bandage main body and dried after having been impregnated with a medicinal agent, and peel paper sheets affixed to the main body to cover the pad and separable therefrom when pulled away from each other. However, these bandages have drawbacks. Although the pad contains a medicinal agent, it is in a dry state, so that the pad is likely to injure the wound and also fails to produce a sterilizing antiseptic effect even when in contact with the wound unless the medicinal agent dissolves out from the pad into the fluid secreted from the wounded portion.

Accordingly first-aid adhesive bandages of another type have been proposed which comprise a container in the form of a capsule or blister provided on a pad and having a medicinal solution enclosed therein, such that when the capsule or blister is depressed from above for use, an aluminum foil or like thin sheet forming the bottom wall of the capsule or blister is ruptured by the pressure of medicinal solution to impregnate the pad with the solution. Nevertheless, when the capsule or blister is depressed to apply a pressure to the solution therein, the pressure of the solution ruptures the weakest portion of the thin sheet, i.e. an outer peripheral portion of the thin sheet where the lower edge of the peripheral wall of the capsule or blister is adhered to the thin sheet. Consequently, the solution is forced out through this portion over the adhesive surface of the bandage main body or off the surface, failing to properly impregnate the pad for use.

Of first-aid adhesive bandages with a container having medicinal agent enclosed therein, those having a blister portion constituting part of the container and integrally united with a peel sheet suffer the following drawbacks. The container and the peel sheet, which can not be separately and freely made of different materials in this case, must be produced from a limited range of materials by a limited mode of methods. Moreover, the peel sheet, which can be a thin sheet made of inexpensive materials such as plastics, paper and the like in separate preparation of the sheet and container, must be prepared from materials which have strength sufficient to hold the medicinal agent and resistance to chemicals for protection from chemical attack by the agent, i.e. expensive materials.

When a container and a peel sheet are separately made, the container is covered with the peel sheet. With this structure, the bandage has the following problems: (i) the peel sheet partly lies as greatly separated from the bandage main body and thus can not remain securely affixed to the adhesive coating of the main body, failing to cover the pad in a manner sufficient to keep it clean; (ii) in rupturing the container by depression from above, the container can not be touched directly with the hand and is likely to move loosely under the peel sheet or on the pad, becoming difficult to properly rupture; and (iii) since with the container so positioned, part of the peel sheet significantly stands out above the bandage main body, making the bandage bulky as a whole; and (iv) when the container is merely laid as interposed between the peel sheet and the pad, it is difficult to securely hold the container in place on the pad.

It is an object of this invention to provide a first-aid adhesive bandage which comprises a bandage main body, a pad affixed to the upper surface or adhesive surface of a bandage main body, at least one peel sheet and a container disposed on or over the pad, the container having a bottom wall made of a thin sheet, such as aluminum foil, and containing a medicinal agent enclosed therein, such that when the bandage is to be used, the thin sheet of the container can be ruptured to properly apply the medicinal agent to the pad or cause the agent to impregnate the pad; it is possible to prepare the peel sheet and the container from different materials by suitable methods; the container is held in place on or over the pad and can be ruptured at its bottom wall by being touched directly with the hand; the peel sheet is securely affixed to the bandage main body and is so provided as to safely protect the pad; and the bandage presents an appearance which is not rendered bulky by the container disposed therein.

The object of this invention can be achieved by a first-aid adhesive bandage comprising a bandage main body having an adhesive coating on its upper surface, a pad affixed to the upper surface of the main body, a container having a medicinal agent enclosed therein and at least one peel sheet temporarily affixed to the adhesive coating of the main body and holding the container in place on or over the pad, the container including a blister portion, a flange extending horizontally outward from the lower end of the blister portion, a bottom wall made of a thin sheet and closing the bottom opening of the blister portion, and a projection extending downward from the central portion of the container top wall for rupturing the thin sheet by depressing the top wall, the blister portion having the medicinal agent enclosed therein, the projection having a lower end in contact or in proximity to the thin sheet, the peel sheet having the container held in place on or over the pad such that the blister portion of the container is exposed above the peel sheet to extend into a side opposed to the pad, the flange of the container is held in contact with the peel sheet and the bottom wall of the container lies on or over the pad.

According to this invention, the bottom wall of the container can be ruptured by the projection of the top wall when the container top wall is depressed by a finger toward the pad, whereby the medicinal agent is properly applied to the pad or caused to impregnate the pad.

According to this invention, the peel sheet and the container are not integrally molded and thus can be separately and freely made of different materials. This means that they can be produced from such an extensive range of materials by such a wide variety of methods as to facilitate the production thereof from suitable materials at low costs.

The blister portion of the container is exposed above the peel sheet while the flange of the container is laid in contact with the peel sheet. As a result, the container is adequately held in place on or over the pad.

Since the peel sheet does not cover the blister portion of the container and the blister portion is projected above the peel sheet, the peel sheet is not laid greatly away from the main body despite the presence of the container while the peel sheet is kept sufficiently and securely fixed to the adhesive coating of the main body, so that the pad is more safely protected by the peel sheet than otherwise.

Because the blister portion of the container is not covered with the peel sheet but exposed as protruded above the peel sheet, the projection for rupturing the thin sheet can be depressed with the container not loosely moved under the peel sheet but fixedly held thereby, permitting the finger to directly touch the container and thus causing the precise rupture of the container.

As the blister portion of the container is not covered with the peel sheet but stands out as exposed above the peel sheet, the bandage presents a simple appearance and eliminates the possibility of becoming bulky, despite the presence of the container, compared with a bandage having a container entirely covered with a peel sheet.

The container, which is not affixed to the adhesive coating of the bandage main body, can be easily removed after stripping off the peel sheet from the bandage main body.

According to one embodiment of this invention, the blister portion of the container extends from the side of the pad through an aperture of the peel sheet into a side opposed to the pad and the flange of the container is interposed between the pad and the outer periphery of the aperture of the peel sheet.

The aperture for the blister portion may be formed in conformity with the outline of the blister portion or may become opened by forcing the blister portion into cutting lines provided in the blister portion.

According to another embodiment of the invention, the peel sheet comprises a lower strip facing the pad and an upper strip superposed on and affixed to the lower strip, the upper strip having an aperture through which the blister portion of the container extends to be exposed on a side opposed to the pad, the lower strip having an opening through which the bottom wall of the container extends to lie on or over the pad, and the flange of the container being interposed between the lower and upper strips.

In any of the embodiments stated above, the thin sheet rupturing projection can be molded from synthetic resin integrally with the container top wall.

Preferably the projection is in the form of an inverted cone or inverted pyramid having a sharp lower (forward) end or inverted frustum, or is semispherical, so as to concentrically act on the thin sheet.

The container top wall may be provided with a substantially flat surface to facilitate the depression of the container top wall. The container can assume a circular, elliptical or like shape. When the pad is rectangular, the container may have a rectangular shape corresponding to the shape of the pad.

The blister portion of the container may be made of materials selected, for example, from polypropylene, polyethylene and like polyolefines, although depending on the kind of the medicinal agent enclosed in the container. The blister portion may be transparent or semi-transparent to see the presence or absence of the medicinal agent from outside.

The pad may comprise an absorbent material affixed to the upper surface of the bandage main body, and a net covering the absorbent material and entirely or partially held at its outer periphery to the adhesive coating of the main body.

The above and other objects, features and advantages of the invention will become apparent from the following description of the invention with reference to the accompanying drawings which are given for illustrative purposes only and to which the invention is not limited. In the drawings:

FIGS. 3, 4 and 5 are perspective views showing other embodiments each with a peel sheet stripped to some extent;

FIG. 6 is a sectional view showing the embodiment of FIG. 5; and

FIG. 7 is an exploded perspective view showing a combination of the strips of peel sheet and the container in the embodiment of FIG. 5.

Figure 1:
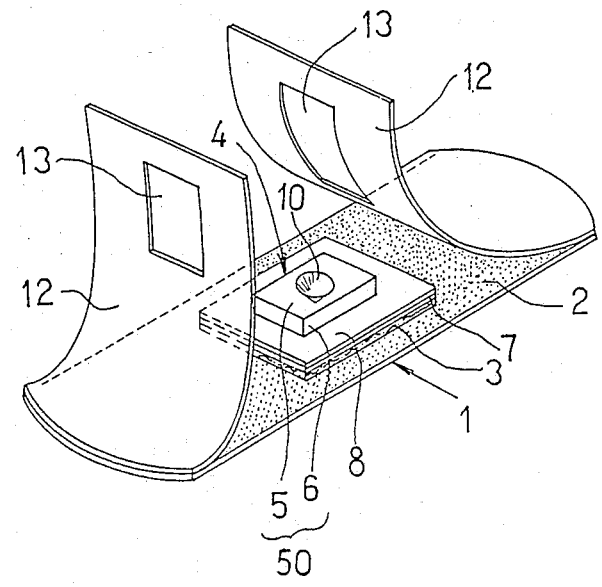
FIG. 1 is a perspective view showing an embodiment of the invention with peel sheets stripped to some extent.
Figure 2:
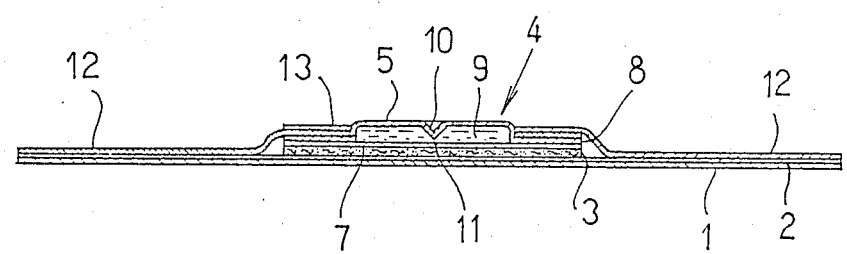
FIG. 2 is a sectional view showing the embodiment of FIG. 1.

With reference to FIGS. 1 and 2, an embodiment of the invention will be described. Indicated at 1 is an adhesive bandage main body in the form of a rectangular adhesive sheet which is prepared by applying an adhesive 2 to the upper surface of a woven or nonwoven fabric, plastics sheet or the like. A pad 3 of gauze, absorbent cotton, nonwoven fabric or the like is affixed to the central portion of the main body 1 on the upper surface thereof.

A container 4 has a blister portion 50 extending from a top wall 5 to a peripheral wall 6 and made of a plastics film piece. The container 4 has at its lower end an opening which is closed with a thin sheet 7 of aluminum foil or glassine paper. The upper surface of the outer peripheral portion of the thin sheet 7 is affixed, with a suitable adhesive or by heat sealing, to the lower surface of a flange 8 made of the plastics film and extending horizontally outward from the lower end of the peripheral wall 6. The container 4 has enclosed therein a chemical solution such as a sterilizing antiseptic solution or a medicinal agent 9 such as analgesic, styptic agent, ointment or the like.

The container 4 is placed on the pad 3 with the thin sheet 7 superposed thereon.

The top wall 5 of the container 4 is formed at its center with a downwardly extending projection 10 in the form of an inverted cone, inverted pyramid or the like and having a V-shaped section. The projection 10 has a sharp lower end 11 positioned close to the center of the upper surface of the thin sheet 7 serving as the bottom wall of the container 4.

A pair of peel sheets 12, 12 chiefly made of paper, synthetic resin or the like is temporarily affixed to the surface of the adhesive coating 2 of the bandage main body 1 at its opposite sides. Rectangular retaining apertures 13, 13 for the container to fit in are formed in the center of the portions of the peel sheets 12, 12 lapping over each other on the container 4. When overlapping each other, these sheets 12, 12 are in contact with the upper surface of the flange 8 of the container 4 to hold the container 4 placed on the pad 3.

When the first-aid adhesive bandage thus constructed is to be used, the top of the container 4 is depressed to slightly bend the top wall 5 downward before or after the peel sheets 12, 12 are stripped off by being pulled away from each other, whereby the projection 10 is brought into contact with the thin sheet 7 and ruptures the sheet 7 with its lower end 11 before the pressure on the medicinal agent 9 acts strongly on the sheet 7. The container top wall 5 in this state is further depressed and deformed, forcing out the medicinal agent 9 from the container through the ruptured portion of the sheet 7, whereby the medicinal agent is caused to impregnate or applied to the central portion of the pad 3.

When the projection 10 in contact with the thin sheet 7 is depressed in this case, the pad 3 backing the thin sheet 7 is compressed by the pressure at its central portion, permitting the portion of the thin sheet 7 pressed on by the projection 10 to be warped downward, with the result that a tensile force acts concentrically on this portion to easily rupture the sheet. Accordingly the lower end of the projection 10 need not always be sharp-pointed but can be circular arc, inverted trapezoidal or otherwise shaped in section as in the embodiments shown in FIGS. 3 and 4. When the lower end of the projection 10 is thus positioned in contact with or in proximity to the thin sheet 7, the thin sheet 7 can be immediately ruptured by the depression of the projection 10.

Figure 3:
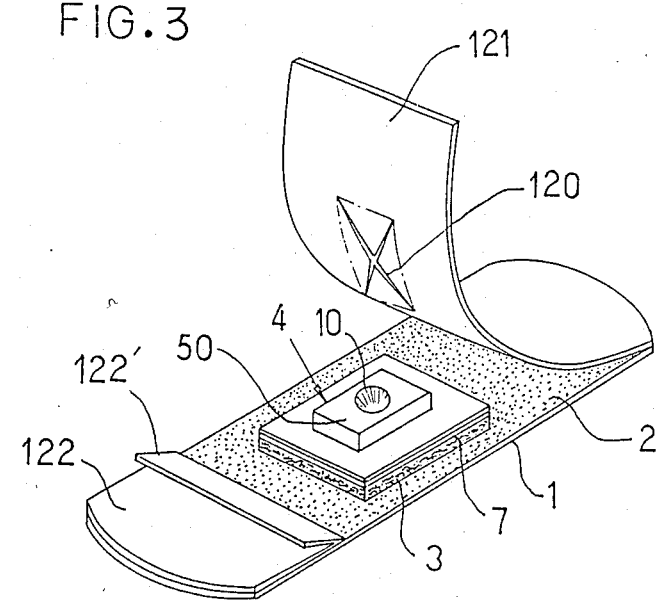

The embodiment of FIG. 3 has the same construction as the one shown in FIGS. 1 and 2 except peel sheets.

According to the embodiment of FIG. 3, one of opposite peel sheets 121, 122, i.e. the peel sheet 121, has a length sufficient to overlap the container 4 and a knob end portion 122' formed by folding back the other peel sheet 122. The sheet 121 has a cross cut 120 for the container 4 to fit into the sheet 121 so that the container 4 extends from the side of the pad, protruding on the other side.

Figure 4:
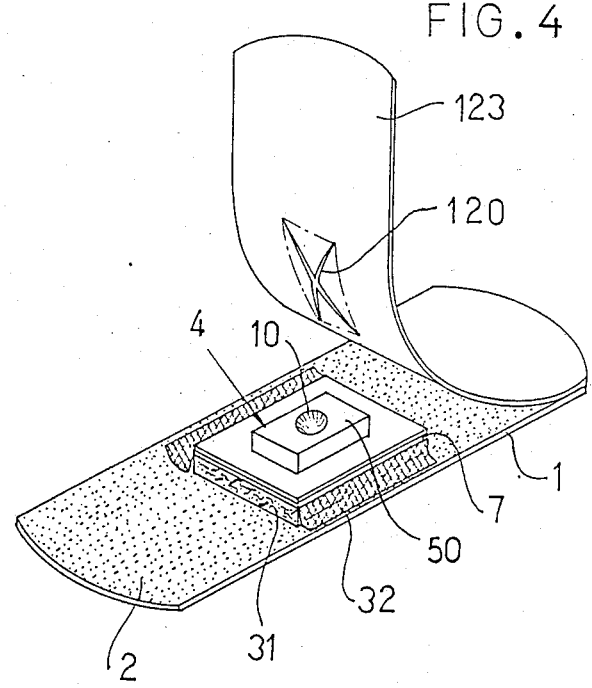

The embodiment of FIG. 4 has the same construction as the one shown in FIGS. 1 and 2 except a peel sheet 123 and its pad.

The pad of the embodiment of FIG. 4 comprises an absorbent material 31 such as absorbent cotton, gauze, nonwoven fabric or the like, and a thin flexible net 32 covering the material 31. The net 32 is held at its peripheral portion to the adhesive 2. The net 32 is made, for example, of polyethylene. The peel sheet 123 has approximately the same length and the same width as the adhesive bandage main body 1 and is formed with a cross cut 120 for the container to fit into the sheet.

According to the embodiment as shown in FIGS. 5, 6 and 7, the first-aid adhesive bandage comprises a bandage main body 1 having an adhesive coating on its upper surface, a pad 3 affixed to the upper surface of the main body, a container 4 having a medicinal agent enclosed therein and a pair of peel sheets 12', 12''. The peel sheets 12', 12'' are temporarily affixed to the adhesive coating of the main body 1 and the peel sheet 12' holds the container 4 in place on or over the pad. The container 4 includes a blister portion 50, a flange 8 extending horizontally outward from the lower end of the blister portion, a bottom wall made of a thin sheet 7 of aluminum foil or like material and closing the bottom opening of the blister portion 50, and a projection 10 extending downward from the central portion of the top wall 5 of the container 4 for rupturing the thin sheet 7 by depressing the top wall 5 toward the thin sheet 7. The blister portion 50 has the medicinal agent 9 enclosed therein. The lower end of the projection 10 is positioned in contact or in proximity to the thin sheet.

The peel sheet 12' consists of a lower strip 121'' facing the pad 3 and an upper strip 121' superposed on and affixed to the lower strip, the upper strip 121' having an aperture 13' through which the blister portion 50 of the container 4 extends to be exposed on a side opposed to the pad 3, the lower strip 121'' having an opening 13'' through which the bottom wall of the container 4 extends to lie on or over the pad, and the flange 8 of the container being interposed between the lower and upper strips 121', 121''.

The embodiment of the invention as shown in FIGS. 5, 6 and 7 has the following advantages. Since the blister portion of the container is projected above the upper strip of the peel sheet and the flange of the container is retained as sandwiched between the upper and lower strips of the peel sheet, the container is fixedly held in place on or over the pad. With the flange securely interposed between the upper and lower strips of the peel sheet, the container, during storage or in rupture of the container bottom, is unlikely to slide on to the adhesive coating of the bandage main body and adhere thereto, eventually deforming the bandage as a whole or becoming difficult to remove after rupture. The container, which is held by the peel sheet, can be readily removed together with the peel sheet, and therefore will not be left fixed to the main body and/or the pad after evacuation of the content.

According to the embodiments described, the container 4 is merely depressed lightly from above, whereby the central portion of the thin sheet 7 can be readily and reliably ruptured by the lower end of the projection 10, causing the medicinal agent 9 within the container 4 to properly spread from the central portion of the pad 3 toward the peripheral portion thereof for application or impregnation.

Further because the projection 10 has its lower end positioned close to or in contact with the thin sheet 7, the thin sheet 7 can be ruptured by the projection 10 before compressive pressure acts on the thin sheet 7 to rupture the same through the medicinal agent 9 within the container 4. Consequently the medicinal agent 9, which is not subjected to a great compressive force when the sheet is ruptured, can be applied to or caused to impregnate the pad 3 gradually or smoothly without flowing out suddenly or scattering. This assures very convenient use.

The foregoing is a description of preferred embodiments of the invention, and it will be understood that various modifications may be made without departing from the spirit of the invention or the scope of the appended claims.

I claim:

1. A first-aid adhesive bandage comprising:
   a bandage main body having an adhesive coating on its upper surface;
   a pad affixed to the upper surface of the main body;
   a container having a medicinal agent enclosed with said container, said container including a blister portion having a bottom opening, a flange extends horizontally outward from the lower end of the blister portion, a flat bottom wall made of a thin sheet closes the bottom opening of the blister portion and encloses said medicinal agent within said blister portion, said bottom wall of the container lying on or over said pad;
   a projection extending downward from the central portion of the container top wall for rupturing the thin sheet of said flat bottom wall by depressing the top wall to apply said medicinal agent to said pad through a rupture in said flat bottom wall, said projection having a lower end in contact with or in proximity to said thin sheet; and
   at least one peel sheet detachably adhered to the adhesive coating of the main body, said peel sheet locating said container in place on or over said pad and holding the container in position on or over the pad such that said blister portion of the container is exposed above the peel sheet to extend into a side opposed to the pad, said flange of the container being held in contact with the peel sheet.

2. A first-aid adhesive bandage according to claim 1 wherein the blister portion of the container extends from the side of the pad through an aperture of the peel sheet into a side opposed to the pad and the flange of the container is interposed between the pad and the outer periphery of the aperture of the peel sheet.

3. A first-aid adhesive bandage according to claim 2 wherein the aperture of the peel sheet is opened in conformity with the outline of the blister portion of the container.

4. A first-aid adhesive bandage according to claim 2 wherein the aperture of the peel sheet becomes opened by forcing the blister portion into cut lines in the peel sheet.

5. A first-aid adhesive bandage according to claim 1 wherein the peel sheet comprises a lower strip facing the pad and an upper strip superposed on and affixed to the lower strip, said upper strip having an aperture through which the blister portion of the container extends to be exposed on a side opposed to the pad, the lower strip having an opening through which the the bottom wall of the container extends to lie on or over the pad, said flange of the container being interposed between said lower and upper strips.

6. A first-aid adhesive bandage according to claim 1 wherein the thin sheet rupturing projection is integral with the top wall of the container.

7. A first-aid adhesive bandage according to claim 1 wherein the projection is in the form of an inverted cone or pyramid.

8. A first-aid adhesive bandage according to claim 1 wherein the top wall of the container is substantially flat.

9. A first-aid adhesive bandage according to caims 1 wherein the container has a rectangular shape.

10. A first aid adhesive bandage according to claim 1 wherein the blister portion of the container is made of a transparent or semitransparent material to allow determination of the presence or absence of the medicinal agent enclosed in the container by visual observation from outside of the container.

11. A first-aid adhesive bandage according to claim 1 wherein the blister portion of the container is made of polyolefine.

12. A first-aid adhesive bandage according to claim 11 wherein the polyolefine is polyethylene.

13. A first-aid adhesive bandage according claim 11 wherein the polyolefine is polypropylene.

14. A first-aid adhesive bandage according to claim 1 wherein the pad comprises an absorbent material affixed to the upper surface of the bandage main body, and a net covering the absorbent material and entirely or partially held at its outer periphery to the adhesive coating of the main body.

* * * * *